(12) United States Patent
Schmitz

(10) Patent No.: US 6,524,630 B2
(45) Date of Patent: Feb. 25, 2003

(54) USE OF COCOA PROCYANIDINS COMBINED WITH ACELYLSALICYCLIC ACID AS AN ANTI-PLATELET THERAPY

(75) Inventor: Harold H. Schmitz, Branchburg, NJ (US)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 09/815,186

(22) Filed: Mar. 22, 2001

(65) Prior Publication Data

US 2002/0022061 A1 Feb. 21, 2002

Related U.S. Application Data

(60) Provisional application No. 60/191,203, filed on Mar. 22, 2000.

(51) Int. Cl.[7] .................. A61K 35/78; A61K 31/60; A61K 31/35
(52) U.S. Cl. ............. 424/776; 424/725; 514/165; 514/453; 514/456
(58) Field of Search ..................... 424/776, 725; 514/165, 453, 456

(56) References Cited

U.S. PATENT DOCUMENTS

| | | | |
|---|---|---|---|
| 4,228,162 A | * | 10/1980 | Luzzi et al. |
| 4,275,059 A | * | 6/1981 | Flora et al. |
| 4,749,575 A | * | 6/1988 | Rotman |
| 4,937,076 A | * | 6/1990 | Lapidus |
| 5,554,645 A | | 9/1996 | Romanczyk, Jr. et al. |
| 5,753,296 A | * | 5/1998 | Girsh |
| 6,086,910 A | | 7/2000 | Howard et al. |
| 6,099,854 A | | 8/2000 | Howard et al. |
| 6,194,020 B1 | * | 2/2001 | Myers et al. |
| 6,297,273 B1 | * | 10/2001 | Romanczyk, Jr. |

FOREIGN PATENT DOCUMENTS

| | | | |
|---|---|---|---|
| JP | 02184626 | * | 7/1990 |
| RU | 2034533 | * | 5/1995 |
| WO | WO 87/04619 | | 8/1987 |
| WO | WO 97/36497 | * | 10/1997 |
| WO | WO 98/11789 | | 3/1998 |
| WO | WO 98/121189 | | 3/1998 |
| WO | WO 99/45797 | | 9/1999 |
| WO | WO 00/06171 | | 2/2000 |
| WO | WO 2001/41775 | * | 6/2001 |

OTHER PUBLICATIONS

Erdman et al. Proceedings of an AAAS symposium held on Feb. 19, 2000—CABA Abstract enclosed.*
Arts et al. 1999. Lancet. vol. 354, p. 488—FSTA Abstract enclosed.*
Charles H. Hennekens, Aspirin in the Treatment and Prevention of Cardiovascular Disease, Ann. Rev. Public Health. 18:37–49, 1997.
M. Putter, et al., Inhibition of Smoking–Induced Platelet Aggregation by Aspirin and Pycnogenol, Thrombosis Research, 95:155–161, 1999.
Heart–Healthy Benefits of Wine, Grape Juice Now in a Supplement; PR:FM PR Newswire, May 13, 1998.
DA Pearson et al. "Effect of Aspirin and Cocoa Procyanidins on Platelet–Dependent Hemostasis" Abstract, 2001, vol. 15, No. 4, p. A 285.

* cited by examiner

Primary Examiner—Christopher R. Tate
(74) Attorney, Agent, or Firm—Clifford Chance US LLP; Margaret B. Kelley

(57) ABSTRACT

The invention relates to the use of cocoa procyanidins in combination with an aspirin as an anti-platelet therapy and compositions comprising cocoa procyanidins and aspirin (acetylsalicyclic acid).

25 Claims, 4 Drawing Sheets

USE OF COCOA PROCYANIDINS COMBINED WITH ACELYLSALICYCLIC ACID AS AN ANTI-PLATELET THERAPY

This application claims priority, under 35 U.S.C. § 119, from the U.S. provisional patent application Ser. No. 60/191,203, filed Mar. 22, 2000, the disclosure of which is hereby incorporated herein by reference.

BACKGROUND OF THE INVENTION

This application is concerned with the use of a combination of cocoa procyanidins and aspirin as an anti-platelet therapy.

A compound consisting of one aromatic ring which contains at least one hydroxyl group is classified as a simple phenol. A polyphenol therefore consists of more than one aromatic ring, each ring containing at least one hydroxyl group. Flavonoids are polyphenols which have a diphenyl propane (C6-C3-C6) skeleton structure, and are found ubiquitously in the plant kingdom. The class of flavonoids called the proanthocyanidins are oligomers of flavan-3-ol monomer units most frequently linked 4→6 or 4→8. One of the most common classes of proanthocyanidins are the procyanidins, which are oligomers of catechin and epicatechin, and their gallic acid esters.

It is known that regular consumption of dietary polyphenols, commonly found in a variety of fruits and vegetables, contributes to a reduction in mortality from cardiovascular disease (CVD), including stroke, heart disease and vascular thrombosis. Red wine, green tea and cocoa have all been identified as being rich in polyphenols, and red wine and green tea have both been shown to be inversely associated with heart disease deaths in industrialized countries.

In addition to reducing the risk of atherogenesis, dietary polyphenols have been shown to have a variety of other potentially beneficial biological activities. For example, they have been shown to inhibit viral reverse transcriptase, inhibit the replication of HIV I in vitro, suppress ulcer formation, and are antimutagenic, neuroprotective, anti-inflammatory, anti-bacterial, hypotensive, and cytotoxic to a variety of cancer cell types.

The mechanisms by which the dietary polyphenols exert their biological functions are not fully understood, but it is known that they have powerful anti-oxidant properties and have an inhibitory effect on platelet activity.

Aspirin (acetylsalicylic acid) is the prototype non-steroidal anti-inflammatory agent. It has been used for many years as an antiplatelet therapy to reduce the risk of recurrent transient ischemic attacks or cerebrovascular accident. The mechanism of action of aspirin is well-defined (Vane, J., Nature, 1971). Put simply, it inhibits the arachidonic acid pathway by causing the alteration of platelet prostaglandin G/H synthase 1, causing the irreversible loss of its cyclooxygenase activity. This results in a decreased conversion of arachidonic acid to the prostaglandins, which are extremely potent mediators of a diverse group of physiological processes. It is the reduced formation of these prostaglandins, in particular thromboxane A2 and prostaglandin E2, which accounts for the variety of pharmacological effects of aspirin that form the basis for its therapeutic use. Unfortunately, the same factors account for the well-documented toxicity of aspirin.

Platelets lack the means with which to synthesize new proteins, which means that the defect caused by aspirin cannot be repaired during the life-span of the platelet. This means that the inhibitory effect of repeated daily doses of aspirin is cumulative, and eventually results in almost complete suppression of platelet thromboxane biosynthesis after 7–10 days. Biochemical, pharmacologic and clinical data support the theory that it is the suppression of thromboxane, leading to a prevention of thromboxane-dependent platelet activation, which accounts for the antithrombotic effects of aspirin.

However, various other prostaglandins produced by the arachidonic acid pathway are responsible for several important homeostatic mechanisms, such as gastric acid secretion, primary hemostasis, control of blood-pressure and renal function. Consequently, long-term aspirin treatment leads to deleterious effects. These include serious gastrointestinal complications, including bleeding and perforation, bleeding complications such as hemorrhagic events, and an increase in the risk of chronic renal disease.

Over the years, an increased understanding of the positive and negative aspects of long-term aspirin treatment has resulted in a downward trend in recommended daily dose, sometimes in combination with low-intensity oral anti-coagulants (in high-risk patients).

Clearly, the discovery of an anti-platelet agent which does not cause the dangerous side-effects of aspirin, and which could either be used to replace aspirin in long-term prevention/treatment regimes, or could be used in tandem with very low doses of aspirin, would be a huge step forward in the treatment and prevention of any disease or disorder caused by platelet dysfunction. Such a discovery would be greeted with great enthusiasm by the medical profession and by members of the public who are either at risk of such disorders or wish to prevent the possibility of such disease occurrence.

SUMMARY OF THE INVENTION

The procyanidins present in cocoa have been shown to have an anti-platelet effect both in vitro and in vivo. It has also been shown that the mechanism of the anti-platelet action is not via inhibition of the arachidonic acid pathway. Additionally, it would appear that treatment with low doses of aspirin in combination with cocoa procyanidins results in an enhanced anti-platelet effect, exceeding the anti-platelet effects of the two individual treatments. Therefore, the invention provides an alternative long-term anti-platelet therapy without the unpleasant and dangerous side-effects associated with aspirin.

DETAILED DESCRIPTION

Figure 1:
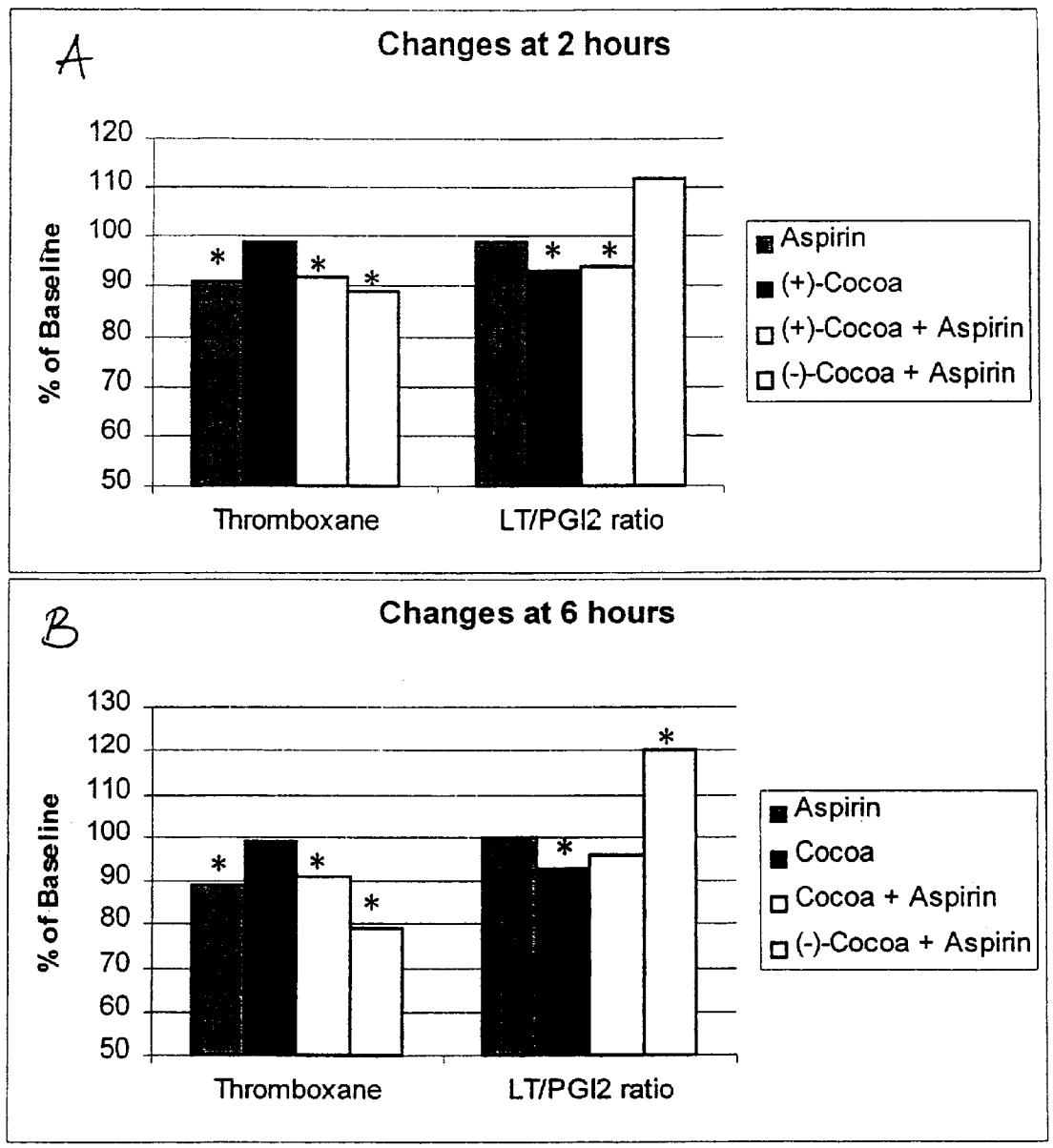
FIG. 1A–B represents comparative thromboxane and LT/PGI2 ratio levels among the four treatments: aspirin, (+)-cocoa, aspirin in combination with (+)-cocoa, and aspirin in combination with (−)-cocoa recorded at two time intervals.

The invention relates to the use of cocoa procyanidins in combination with an aspirin as an anti-platelet therapy and compositions comprising cocoa procyanidins and aspirin (acetylsalicyclic acid).

As used herein, "cocoa procyanidins" are monomers and/or oligomers of epicatechin and catechin. The term "procyanidin" has also been used in the art with a more limiting meaning, i.e., to refer to oligomers (but not monomers) of epicatechin and catechin. However, for brevity, the term is used herein to encompass the monomers as well as the oligomers.

The invention relates to a composition comprising an aspirin and a cocoa procyanidin. The composition may be presented via any suitable form but is typically formulated as a pharmaceutical composition, a food, a dietary supplement or a food additive.

In one embodiment, the present invention provides a composition suitable for ingestion comprising, in a physiologically acceptable carrier, aspirin and a cocoa procyanidin. The composition may be presented via any suitable form but is typically formulated as a pharmaceutical composition, a food, a dietary supplement or a food additive.

The present invention also provides:
Use of aspirin and a cocoa procyanidin in the manufacture of a medicament, food, dietary supplement or food additive for the treatment or prevention of a disease or disorder caused by platelet dysfunction (such as a pathological activation of platelets contrast to the normal platelet activation that leads to clot formation and prevention of bleeding);
Use of aspirin in the manufacture of a medicament, food, dietary supplement or food additive for use with a cocoa procyanidin in the prevention or treatment of a disease or disorder caused by platelet dysfunction; and
Use of a cocoa procyanidin in the manufacture of a medicament, food, dietary supplement or food additive for use with aspirin in the prevention or treatment of a disease or disorder caused by platelet dysfunction.

Cocoa polyphenols include cocoa procyanidins, which are monomers and/or oligomers of epicatechin and catechin.

Procyanidin monomers have the structure:

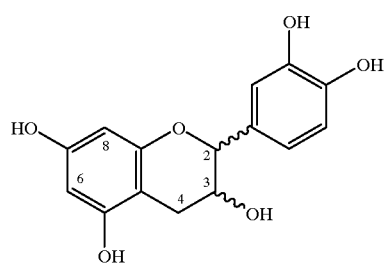

Procyanidins include those found in cocoa beans obtained from Theobroma cacao and various related cocoa species, as well as the genus Herrania and their inter- and intra-genetic crosses.

Procyanidin monomers include (+)-catechin, (−)-epicatechin and their respective epimers (e.g. (−)-catechin and (+)-epicatechin).

Synthetic linear and/or branched oligomers having the following structures are illustrative of the cocoa procyanidins.

Linear oligomers where n is an integer from 0 to 16

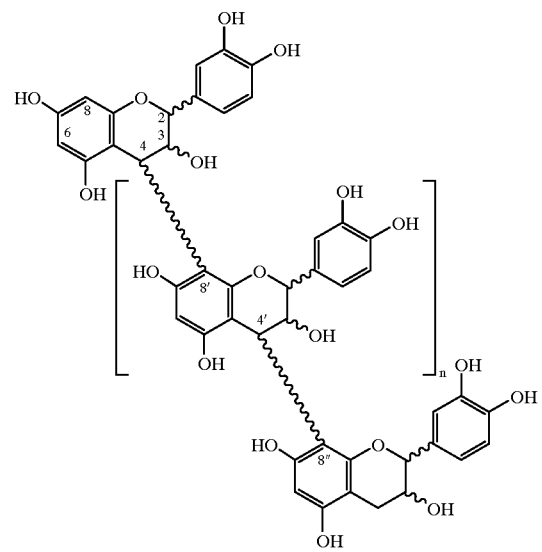

Branched oligomers where A and B are independently oligomers from 1 to 15 which total 3–18 in final oligomer.

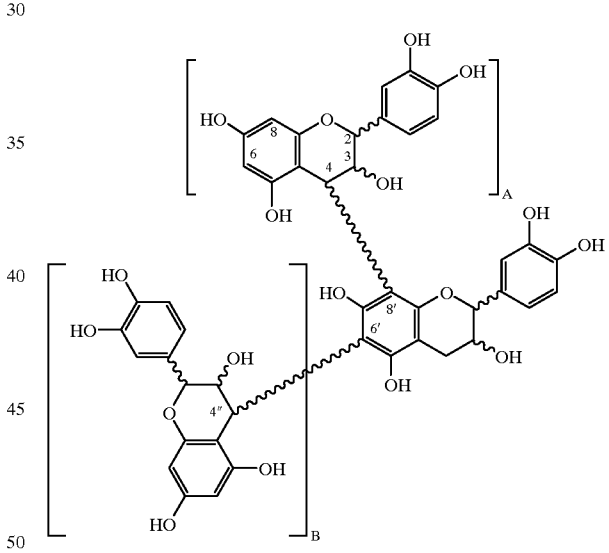

In the oligomers n is an integer from 2 through 18, preferably 3 through 12, more preferably 5 through 12, and most preferably 5. The oligomers have interflavan linkages of (4→6) and and/or (4→8). The oligomers may be represented by the structures above. For the linear oligomer, when x is 0, the oligomer is termed a "dimer"; when x is 1 the oligomer is termed a "trimer"; when x is 2, the oligomer is termed a "tetramer"; when x is 3, the oligomer is termed a "pentamer"; and similar recitations may be designated for oligomers having x up to and including 18 and higher, such that when x is 18, the oligomer is termed an "octadecamer." For the branched oligomer, when A or B is 1, the oligomer is termed a "trimer"; with similar recitations such as those described for the linear oligomers.

The cocoa procyanidins can be provided by cocoa ingredients, especially cocoa ingredients having an enhanced content of cocoa procyanidins, or they can be prepared synthetically. Cocoa ingredients are any substances obtainable from cocoa beans which contain cocoa procyanidins and include, for instance, chocolate liquor, cocoa butter, partially defatted cocoa solids and/or fully defatted cocoa solids. The cocoa procyanidins can be used in the form of cocoa ingredients or they can be extracted from cocoa beans, cocoa nibs, or cocoa ingredients, such as those mentioned above.

Methods for cocoa polyphenol content are described in U.S. Pat. No. 5,554,645 (issued Sep. 10, 1996) which is hereby incorporated herein by reference. Harvested cocoa pods were opened and the beans with pulp were removed for freeze-drying. The pulp was manually removed from the freeze-dried mass and the beans were subjected to the following manipulations. The freeze-dried cocoa beans were first manually dehulled and ground to a fine powdery mass with a TEKMAR Mill. The resultant mass was then defatted overnight by Soxhlet extraction using redistilled hexane as the solvent. Residual solvent was removed from the defatted mass by vacuum at ambient temperature.

Cocoa polyphenols, including cocoa procyanidin monomers and/or oligomers, can also be extracted from fresh cocoa beans, cocoa nibs, or cocoa nib fractions preferably from unfermented, underfermented cocoa beans which contain higher levels of cocoa polyphenols. They can also be extracted from chocolate liquor, partially defatted cocoa solids, and/or fully defatted cocoa solids which preferably have a high cocoa polyphenol content. A solvent which dissolves the cocoa polyphenols, including the procyanidins, is used.

In one aspect of the present invention, therefore, the cocoa procyanidin is an oligomer, monomer or mixture thereof, which oligomer, monomer or mixture is obtainable by (a) subjecting defatted ground cocoa nibs, cocoa nib fractions, chocolate liquor, partially defatted cocoa solids or fully defatted cocoa solids to solvent extraction with a solvent in which cocoa procyanidins are soluble; and (b) isolating a fraction comprising the or each procyanidin monomer, oligomer or mixture from the resulting cocoa extract.

Suitable solvents include water, methanol, ethanol, acetone, ethyl acetate, or mixtures thereof. Preferred solvents are mixtures of water and methanol or acetone. A preferred extraction procedure is two extractions with acetone/water/acetic acid (70%:29.5%:0.5%) followed by a third extraction with methanol:water:acetic acid (70%:29.5%:0.5%). Preferably the solvent(s) are slightly acidified. In some cases the extract is purified, for example by removal of the caffeine and/or theobromine, and then further purified by gel permeation chromatography and/or high pressure liquid chromatography. During the high pressure liquid chromatography, the extract can be fractionated into monomeric and oligomeric fractions containing at least 50% by weight of the monomers or specific oligomers. When the fractions contain the monomers and lower oligomers (up to and including the tetramer), the fractions contain about 90 to 95% by weight of the particular oligomeric fraction.

In another embodiment, cocoa polyphenols, typically cocoa procyanidin monomers and/or oligomers, are present in a cocoa ingredient (for instance as described above) having an enhanced or conserved level of cocoa polyphenols. An enhanced level of cocoa polyphenols may be achieved by adding cocoa polyphenols, for instance cocoa procyanidin monomers, oligomers and/or mixtures thereof, to the cocoa ingredient. A conserved level of cocoa polyphenols may be achieved by controlling the degree of fermentation of the cocoa beans since as discussed below, the cocoa polyphenol content, including the cocoa procyanidin content, of roasted cocoa nibs, chocolate liquor, and partially defatted or nonfat cocoa solids is higher when these are prepared from cocoa beans or blends thereof which are underfermented.

A conserved level of cocoa polyphenols may also be achieved by controlling the conditions under which the beans are processed. Thus, a method of producing cocoa butter and/or cocoa solids having conserved levels of cocoa polyphenols from cocoa beans uses a unique combination of processing steps which does not require separate bean roasting or liquor milling equipment, allowing for the option of processing cocoa beans without exposure to severe thermal treatment for extended periods of time and/or the use of solvent extraction of fat. The benefit of this process lies in the enhanced conservation of polyphenols in contrast to that found in traditional cocoa processing, such that the ratio of the initial amount of polyphenol found in the unprocessed bean to that obtainable after processing is less than or equal to 2.

Partially defatted cocoa solids having a high cocoa polyphenol content, including a high cocoa procyanidin content, can be obtained by processing the cocoa beans directly to cocoa solids without a bean or nib roasting step. This method conserves the cocoa polyphenols because it omits the traditional roasting step. This method consists essentially of the steps of: (a) heating the cocoa beans to an internal bean temperature just sufficient to reduce the moisture content to about 3% by weight and to loosen the cocoa shell; (b) winnowing the cocoa nibs from the cocoa shells; (c) screw pressing the cocoa nibs; and (d) recovering the cocoa butter and partially defatted cocoa solids which contain cocoa polyphenols including cocoa procyanidins. Optionally, the cocoa beans are cleaned prior to the heating step, e.g., in an air fluidized bed density separator. The winnowing can also be carried out in the air fluidized bed density separator. Preferably, the cocoa beans are heated to an internal temperature of about 100° C. to about 110° C., more preferably less than about 105° C., typically using an infra red heating apparatus for about 3 to 4 minutes. If desired, the cocoa solids can be alkalized and/or milled to a cocoa powder.

The internal bean temperature (IBT) can be measured by filling an insulated container such as a thermos bottle with beans (approximately 80–100 beans). The insulated container is then appropriately sealed in order to maintain the temperature of the sample therein. A thermometer is inserted into the bean-filled insulted container and the temperature of the thermometer is equilibrated with respect to the beans in the thermos. The temperature reading is the IBT temperature of the beans. IBT can also be considered the equilibrium mass temperature of the beans.

Cocoa beans can be divided into four categories based on their color: predominately brown (fully fermented), purple/brown, purple, and slaty (unfermented). Preferably, as indicated above, the cocoa solids are prepared from underfermented cocoa beans which have a higher cocoa polyphenol content than fermented beans. Underfermented beans include slaty cocoa beans, purple cocoa beans, mixtures of slaty and purple cocoa beans, mixtures of purple and brown cocoa beans, or mixture of slaty, purple, and brown cocoa beans. More preferably, the cocoa beans are slaty and/or purple beans. Underfermented beans typically have a fermentation factor of 275 or less.

The "fermentation factor" is determined using a grading system for characterizing the fermentation of the cocoa beans. Slaty is designated 1, purple is 2, purple/brown is 3, and brown is 4. The percentage of beans falling within each category is multiplied b the weighted number. Thus, the "fermentation factor" for a sample of 100% brown beans would be 100×4 or 400, whereas for a 100% sample of purple beans it would be 100×2 or 200. A sample of 50% slaty beans and 50% purple beans would have a fermentation factor of 150 (50×1)+(50×2).

In one embodiment, derivatives of cocoa procyanidins, for example gallated and methylated procyanidins, may be used in combination with aspirin. Any reference herein with respect to the cocoa procyanidins and their uses is also applicable to procyanidin derivatives. Gallated procyanidins may be prepared as described in the International Pat. Appl. No. PCT/US98/21392, published as WO 99/19319. Methylated procyanidins may be prepared as described, for example, in Example 6.

In one aspect of the invention the methylated procyanidin monomer or oligomer is of formula $(A)_n$ wherein n is 1 to 18 and A is a monomer unit of formula:

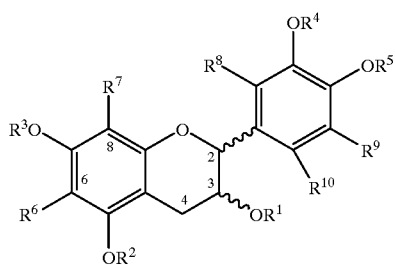

wherein each of $R^1$ to $R^5$, and $R^8$ to $R^{10}$ which are the same or different, is H or $CH_3$; and $R^6$ and $R^7$, which are the same or different, are H, $CH_3$, or a link to an adjacent monomer unit; provided that at least one of groups $R^1$ to $R^{10}$ in at least one monomer unit is $CH_3$. The monomers may, for example, be linked via any one or two of ring positions 4, 6, and 8 by interflavan linkages described above.

In another aspect of the invention, the methylated procyanidin monomer or oligomer is of formula $(A')_n$ wherein n is 1 to 18 and A' is a monomer unit of formula:

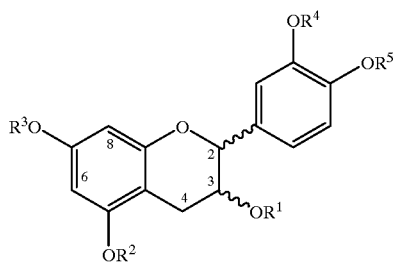

wherein each of $R^1$ to $R^5$, which are the same or different, is H or $CH_3$, provided that at least one of groups $R^1$ to $R^5$ in at least one monomer unit is $CH_3$. The monomers may, for example, be linked via any one or two of ring positions 4, 6, and 8 by interflavan linkages described above.

For example, the oligomer may be a linear oligomer of the following structure wherein n is from 0 to 16:

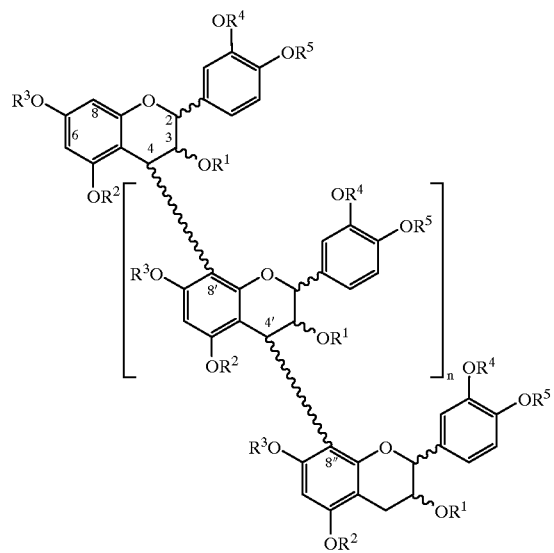

wherein $R^1$ to $R^5$ is as defined above.

Alternatively, or in addition, the oligomer may be a branched oligomer of the following structure wherein A and B are independently oligomers from 1 to 15 which total 3–18 in final oligomer:

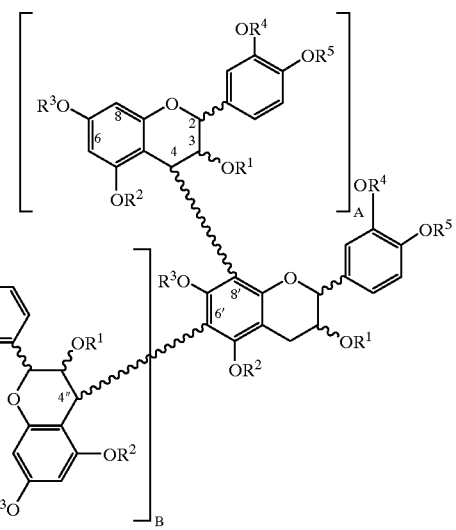

wherein $R^1$ to $R^5$ is as defined above.

In another embodiment, the invention provides a procyanidin oligomer or mixture of oligomers, wherein the or each said oligomer is a methylated tetramer.

For example, the methylated tetramer is a compound of formula $(A)_4$ wherein A is a monomer unit of formula:

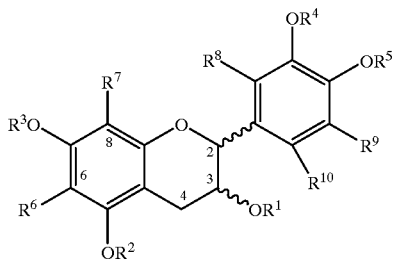

wherein each of $R^1$ to $R^5$, and $R^8$ to $R^{10}$ which are the same or different, is H or $CH_3$; and $R^6$ and $R^7$, which are the same or different, are H, $CH_3$, or a link to an adjacent monomer unit; provided that at least one of groups $R^1$ to $R^{10}$ in at least one monomer is $CH_3$. The monomers may, for example, be linked via any one or two of ring positions 4, 6, and 8 by interflavan linkages described above.

The methylated tetramer may alternatively be a compound of formula $(A')_4$ wherein A is a monomer unit of formula:

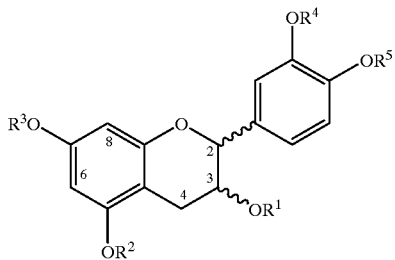

wherein each of $R^1$ to $R^5$, which are the same or different, is H or $CH_3$, provided that at least one of groups $R^1$ to $R^5$ in at least one monomer unit is $CH_3$. The monomers may, for example, be linked via any one or two of ring positions 4, 6, and 8 by interflavan linkages described above.

A methylated cocoa procyanidin tetramer or mixture of tetramers of the invention is obtainable by methylating an isolated fraction of a cocoa extract containing procyanidin tetramers or a synthetically prepared tetramer. For example, the tetramer may be of formula $(A)_4$ as shown above.

In one embodiment, a methylated cocoa procyanidin tetramer or mixture of tetramers, which tetramer or mixture thereof is obtainable by:
  (a) subjecting defatted ground cocoa nibs, cocoa nib fractions, chocolate liquor, partially defatted cocoa solids or fully defatted cocoa solids to solvent extraction with a solvent in which cocoa procyanidins are soluble;
  (b) isolating a fraction containing procyanidin tetramers from the resulting cocoa extract; and
  (c) methylating the isolated fraction.

The methylated cocoa procyanidin oligomer or mixture of oligomers, which oligomer or mixture may also be obtainable by:
  (a) subjecting defatted ground cocoa nibs, cocoa nib fractions, chocolate liquor, partially defatted cocoa solids or fully defatted cocoa solids to solvent extraction with a solvent in which cocoa procyanidins are soluble;
  (b) isolating a fraction containing procyanidin oligomers from the resulting cocoa extract; and
  (c) methylating the isolated fraction.

The composition of the invention is in a form suitable for oral delivery, such as tablets, capsules, pills, concentrates, powders, liquids, solutions or suspensions. It is preferably presented as a pharmaceutical composition, food, dietary supplement or food additive. It may also take the form of a pet food ingredient. The composition may be provided in unit dosage form.

The active compounds can be formulated for immediate or slow-release. A tablet may comprise an effective amount of cocoa polyphenol, cocoa procyanidin monomers and/or oligomers or a cocoa polyphenol-or cocoa procyanidin-containing composition combined with an effective amount of aspirin, and optionally a carrier or release system. Synthetic polymers are particularly useful in the formulation of a composition having controlled release. The capsule may comprise a gelatin capsule containing a predetermined dosage of the cocoa polyphenol and aspirin-containing composition. The oral delivery product may also comprise a dietary supplement nutrient such as dicalcium phosphate, magnesium stearate, calcium nitrate, vitamins, and minerals. Formulations of the cocoa procyanidin/aspirin combinations and compositions containing them can be prepared with standard techniques well known to those skilled in the pharmaceutical, food science, medical and veterinary arts.

The composition is formulated to deliver a combined effective dose of the cocoa procyanidin(s) and aspirin. The effective amount of the cocoa procyanidin can be administered in a single dose or, alternatively, two to three times a day. The daily effective amount for a human is at least 50 mg, preferably 100 mg, and more preferably 150 mg of the cocoa procyanidins. The upper dosage is not limiting. For example, procyanidins can be administered in the range of about 50 to about 1000 mg, about 100 to about 800 mg, about 300 to about 600 mg, or using these lower range dosages without upper dosage limitations, for example, at least 50, 100 or 300 mg/ml. When used with a veterinary animal such as a feline, an equine, or a canine, a person of skill in the art can determine the effective amount from the above dosages taking in consideration, for example, the weight of the animal. The amount of procyanidins can be determined by the methods described in Adamson et al. ("HPLC Method for the Quantification of Procyanidins in Cocoa and Chocolate Samples and Correlation to Total Antioxidant Capacity" J. Ag. Food Chem., Vol. 7:10, 4184–4188), the relevant portion of which is hereby incorporated herein by reference. Due to the enhanced effects achieved when administered in combination with cocoa procyanidins, aspirin may be administered at a lower dose than is required when aspirin is used alone in anti-platelet therapy to achieve cardiovascular protective effects, which is for example, about 80 mg/day for a human. Thus, in the methods and/or compositions of the invention, aspirin may be used in the amount less than about 80 mg/day, for example, from about 10 to about 80 mg/day and preferably from about 20 to about 80 mg/day. In another embodiments, aspirin may be administered at from about 40 to about 80 mg/day, or when administered at less than about 70 mg/day, from about 20 to about 70 mg/day, or from about 30 to about 70 mg/day.

Besides being combined in a single, orally administrable composition, the cocoa procyanidin(s) and aspirin may be formulated for separate administration. Accordingly the present invention further provides a product comprising aspirin and a cocoa procyanidin for separate, simultaneous or sequential use in the treatment of a disease or disorder caused by platelet dysfunction. When administered separately, the cocoa procyanidin and aspirin must be administered within a time period which ensures that they are simultaneously present in the mammal at sufficient concentrations to have a combined effect. A person of skill in the art can determine this time period based on the knowledge of the bioavailability of cocoa procyanidins and aspirin. For example, the cocoa procyanidins and aspirin should be administered to the mammal within 8 hours of one another, preferably within 6 hours of one another, and more preferably within two hours of one another.

The cocoa polyphenol is typically present in a cocoa ingredient having an enhanced or conserved level of cocoa polyphenols, achieved for instance as described above. Thus, in one aspect the cocoa ingredient comprises cocoa solids which are obtainable by:

(a) heating cocoa beans to an internal bean temperature which is just sufficient to reduce the moisture content to about 3% by weight and to loosen the cocoa shell;

(b) winnowing the cocoa nibs from the cocoa shells;

(c) screw pressing the cocoa nibs; and (d) recovering the cocoa butter and partially defatted cocoa solids which contain cocoa polyphenols.

In a preferred embodiment the cocoa ingredient having an enhanced or conserved level of cocoa polyphenols is contained in a beverage mix to be made up into a beverage for co-administration with an effective amount of aspirin. A preferred beverage or beverage mix comprises: high cocoa polyphenol solids and/or cocoa extract; and optionally a natural or artificial sweetener, a natural or synthetic flavorant, and a dairy product. The beverage may also be a carbonated beverage. The sweetener may be a sugar syrup, solids, or a sugar substitute. The term "sugar substitute" includes bulking agents, sugar alcohol (i.e polyols such as glycerol), high potency sweeteners or combinations thereof. Nutritive carbohydrate sweeteners with varying degrees of sweetness intensity may be any of those typically used in the art and include, but are not limited to, sucrose, dextrose, fructose, lactose, maltose, glucose syrup solids, corn syrup solids, invert sugar, hydrolyzed lactose, honey, maple sugar, brown sugar, molasses and the like. Sugar substitutes may partially or totally replace the nutritive carbohydrate sweetener. High potency sugar substitutes include aspartame, cyclamates, saccharin, acesulfame-K, neohesperidin, dihydrochalcone, sucralose, alitame, stevia sweeteners, glycyrrhizin, thaumatin and the like as well as mixtures thereof. Exemplary sugar alcohols include those typically used in the art such ax sorbitol, mannitol, xylitol, maltitol, isomalt, lactitol and the like. Exemplary dairy components are non-fat milk solids, milk fat, sweet cream, butter milk and skim milk.

For the purposes of this application, the following definitions will enable a clearer understanding of what is disclosed and claimed:

As used herein a "food" is a material consisting essentially of protein, carbohydrate and/or fat, which is used in the body of an organism to sustain growth, repair and vital process and to furnish energy. Foods may also contain supplementary substance such as minerals, vitamins and condiments. See Merriam-Webster's Collegiate Dictionary, $10^{th}$ Edition, 1993.

As used herein, a "pharmaceutical" or "medicament" is a medicinal drug. See Merriam-Webster's Collegiate Dictionary, $10^{th}$ Edition, 1993.

As used herein, a "food supplement" or "dietary supplement" is a product (other than tobacco) that is intended to supplement the diet that bears or contains the one or more of the following dietary ingredients: a vitamin, a mineral, an herb or other botanical, an amino acid, a dietary substance for use by man to supplement the diet by increasing the total daily intake, or a concentrate, metabolite, constituent, extract or combination of these ingredients. See Merriam-Webster's Collegiate Dictionary, $10^{th}$ Edition, 1993.

As used on food labels, "supplement" typically means that nutrients have been added in amounts greater than 50% above the U.S. RDA ("Understanding Normal and Clinical Nutirition, Third Edition", Eds. Whitney, Cataldo and Rolfes, p. 525).

For treatment or prevention of any disorder or disease caused by platelet dysfunction, a cocoa procyanidin or mixture of cocoa procyanidin monomers and/or oligomers or a composition comprising cocoa procyanidin or monomers and/or oligomers, in combination with an effective amount of aspirin, alone or with other treatments, may be administered (to a human or a veterinary animal such as a pet animal) as desired by the skilled medical practitioner, according to methods incorporated in this disclosure and known in the art. For example, treatment involving the co-administration of aspirin and cocoa procyanidins may be administered at the first signs or symptoms of platelet dysfunction, or as soon thereafter as desired by the skilled medical practitioner, without any undue experimentation required. Thus, the composition and treatments of the invention may be used, for example, with the subjects suffering from, or at risk of, cardiovascular disease, which includes heart attack, stroke, and peripheral vascular diseases, peripheral artery disease, coronary artery disease, carotid artery disease, atherosclerosis, restenosis.

The co-administration of the cocoa procyanidins and the aspirin, or a composition thereof, alone or with other treatment, may be continued as a regimen, e.g., monthly, bimonthly, biannually, annually, or in some other regimen, by skilled medical practitioner for such time as is necessary, without undue experimentation required.

Further, within the scope of the invention is a package comprising a food, a dietary supplement or a pharmaceutical and a label indicating an enhanced content of cocoa polyphenols including cocoa procyanidins in combination with aspirin, or indicating the beneficial properties of these compounds and, optionally, instructions for use. As used herein, the beneficial properties include the inhibition of platelet dysfunction, for example, in the prevention and treatment of cardiovascular disease and diseases and disorders caused by inflammation.

The invention is further described in the following non-limiting examples.

EXAMPLE 1

Analytical Methods for the Quantification of Cocoa Procyanidins

The analytical method described below was used to separate and quantify, by degree of polymerization, the procyanidin composition of the seeds from *Theobroma cacao* and of chocolate. The analytical method described below is based upon work reported in Hammerston, J. F., Lazarus, S. A., Mitchell, A. E., Rucker R., Schmitz, H. H., *Identification of Procyanidins in Cocoa (Theobroma cacao) and Chocolate Using High-Performance Liquid Chromatography/Mass Spectrometry*, J. Ag. Food Chem.; 1999; 47 (10) 490–496. The utility of the analytical method described below was applied in a qualitative study of a broad range of food and beverage samples reported to contain various types of proanthocyanidins, as reported in Lazarus, S. A., Adamson, G. E., Hammerstone, J. F., Schmitz, H. H., High-performance Liquid Chromatography/Mass Spectrometry Analysis of Proanthocyanidins in Foods and Beverages, J. Ag Food Chem.; 1999; 47 (9); 3693–3701. The analysis in Lazarus et al. (1999) reported analysis using fluorescence detection because of higher selectivity and sensitivity.

Composite standard stock solutions and calibration curves were generated for each procyanidin oligomer through decamer using the analytical method described below, as reported in Adamson, G. E., Lazarus, S. A., Mitchell, A. E., Prior, R. L., Cao, G., Jacobs, P. H., Kremers, B. G., Hammerston, J. F., Rucker, R., Ritter, K.A., Schmitz, H. H., HPLC Method for the Quantification of Procyanidins in Cocoa and Chocolate Samples and Correlation to Total Antioxidant Capacity, J. Ag. Food Chem.; 1999; 47 (10) 4184–4188. Samples were then compared with the composite standard to accurately determine the levels of procyanidins.

Extraction

The fresh seeds (from Brazilian cocoa beans) were ground in a high-speed laboratory mill with liquid nitrogen until the particle size was reduced to approximately 90 microns. Lipids were removed from 220 grams (g) of the ground seeds by extracting three times with 1000 milliliters (mL) of hexane. The lipid free solids were air dried to yield approximately 100 g of fat-free material. A fraction containing procyanidins was obtained by extracting with 1000 mL of 70% by volume acetone in water. The suspension was centrifuged for 10 minutes at 1500 g. The acetone layer was decanted through a funnel with glass wool. The aqueous acetone was then re-extracted with hexane (~75 mL) to remove residual lipids. The hexane layer was discarded and the aqueous acetone was rotary evaporated under partial vacuum at 40° C. to a final volume of 200 mL. The aqueous extract was freeze dried to yield approximately 19 g of acetone extracted material.

Gel Chromatography

Approximately 2 g of the acetone extract (obtained above) was suspended in 10 mL of 70% aqueous methanol and centrifuged at 1500 g. The supernatant was semi-purified on a Sephadex LH-20 column (70×3 centimeters) which had previously been equilibrated with methanol at a flow rate of 3.5 mL/min. Two and a half hours after sample loading, fractions were collected every 20 minutes and analyzed by HPLC for theobromine and caffeine. See Clapperton, J., Hammerstone, J. F., Romanczyk, L. J., Yow, S., Lim, D., Lockwood, R., Polyphenols and Cocoa Flavour, Proceedings, 16th International Conference of Groupe Polyphenols, Lisbon, Portugal, Groupe Polyphenols: Norbonne, France, 1992; Tome II, pp. 112–115. Once the theobromine and caffeine were eluted off the column (~3.5 hours), the remaining eluate was collected for an additional 4.5 hours and rotary evaporated under a partial vacuum at 40° C. remove the organic solvent. Then the extract was suspended in water and freeze dried.

Purification of Procyanidin Oligomers by Preparative Normal-Phase HPLC

The cocoa extract from above (0.7 g) was dissolved in (7 mL) mixture of acetone/acetic acid in a ration by volume of 70:29.5:0.5, respectively. A linear gradient (shown in the table below) was used to separate procyanidin fractions using a 5 μm Supelcosil LC column (Silica, 100 Angstroms (Å); 50×2 cm) (Supelco, Inc., Bellefonte, Pa.) which was monitored by UV at a wavelength of 280 nanometers (nm).

| time (minutes) | methylene chloride/ acetic acid/water (96:2:2 v/v) (%) | methanol/ acetic acid/water (96:2:2 v/v) (%) | Flow rate (mL/min) |
|---|---|---|---|
| 0 | 92.5 | 7.5 | 10 |
| 10 | 92.5 | 7.5 | 40 |
| 30 | 91.5 | 8.5 | 40 |
| 145 | 78.0 | 22.0 | 40 |
| 150 | 14.0 | 86.0 | 40 |
| 155 | 14.0 | 86.0 | 50 |
| 180 | 0 | 100 | 50 |

Fractions were collected at the valleys between the peaks corresponding to oligomers. Fractions with equal retention times from several preparative separations were combined, rotary ed under partial vacuum and freeze dried.

Analysis of Purified Fractions by HPLC/MS

To determine purity of the individual oligomeric fractions, an analysis was performed using a normal-phase high-performance chromatograph (HPLC) method interfaced with online mass spectrometry (MS) analysis using an atmospheric pressure ionization electrospray (API-ES) chamber as described by Lazarus et al. (1999), supra. Chromatographic analyses were performed on an HP 1100 series (Hewlett-Packard, Palo Alto, Calif.) equipped with an auto-injector, quaternary HPLC pump, column heater, diode array detector, and HP ChemStation for data collection and manipulation. Normal-phase separations of the procyanidin oligomers were performed on a Phenomenex (Torrance, Calif.) Luna silica column (25×4.6 mm) at 37° C. UV detection was recorded at a wavelength of 280 nm. The ternary mobile phase consisted of (A) dichloromethane, (B) methanol, and (C) acetic acid and water (1:1 v/v). Separations were effected by a series of linear gradients of B into A with a constant 4% of (C) at a flow rate of 1 mL/min as follows: elution starting with 14% of (B) into (A); 14–28.4% of (B) into (A), 0–30 min; 28.4–50% of (B) into (A), 30–60 mm; 50–86% of (B) into (A), 60–65 min; and 65–70 isocratic.

HPLC/MS analyses of purified fractions were performed using an HP 1100 series HPLC as described above and interfaced to an HP series 1100 mass selective detector (model G1946A) equipped with an API-ES ionization chamber. The buffering reagent was added via a tee in the eluant stream of the HPLC just prior to the mass spectrometer and delivered with an HP 1100 series HPLC pump, bypassing the degasser. Conditions for analysis in the negative ion mode included 0.75 M ammonium hydroxide as a buffering reagent at a flow rate of 0.04 mL/min, a capillary voltage of 3 kV, a fragmentor at 75 V, a nebulizing pressure of 25 psig, and a drying gas temperature at 350° C. Data were collected on an HP ChemStation using both scan mode and selected ion monitoring (SIM). Spectra were scanned over a mass range of m/z 100–3000 at 1.96 seconds per cycle. The ammonium hydroxide was used to adjust the eluant pH to near neutrality via an additional auxiliary pump just prior to entering the MS. This treatment counteracted the suppression of negative ionization of the (−)-epicatechin standard due to the elevated concentration of acid in the mobile phase. The purity for each fraction was determined by peak area, using UV detection at a wavelength of 280 nm in combination with a comparison of the ion abundance ratio between each oligomeric class.

Quantification of Procyanidins in Cocoa and Chocolate

A composite standard was made using commercially available (−)-epicatechin for the monomer. Dimers through decamers were obtained in a purified state by the methods described above. Standard stock solutions using these compounds were analyzed using the normal-phase HPLC method described above with fluorescence detection at excitation and emission wavelengths of 276 nm and 316 nm, respectively. Peaks were grouped and their areas summed to include contributions from all isomers within any one class of oligomers and calibration curves generated using a quadratic fit. Monomers and small oligomers had almost linear plots which is consistent with prior usage of linear regression to generate monomer-based and dimer-based calibration curves.

These calibration curves were then used to calculate procyanidin levels in samples prepared as follows: First, the cocoa or chocolate sample (about 8 grams) was de-fatted using three hexane extractions (45 mL each). Next, one gram of de-fatted material was extracted with 5 mL of the acetone/water/acetic acid mixture (70:29.5:0.5 v/v). The quantity of procyanidins in the de-fatted material was then determined by comparing the HPLC data from the samples with the calibration curves obtained as described above (which used the purified oligomers). The percentage of fat for the samples (using a one gram sample size for chocolate or one-half gram sample size for liquors) was determined using a standardized method by the Association of Official Analytical Chemists (AOAC Official Method 920.177). The quantity of total procyanidin levels in the original sample (with fat) was then calculated. Calibration was performed prior to each sample run to protect against column-to-column variations.

EXAMPLE 2

Clinical Studies

Sixteen subjects were recruited to participate in a randomized clinical trial which involved the consumption of aspirin, a high procyanidin beverage or a combination of the two. Subjects were free from known disease, non-smokers, and were between 20 and 55 years of age. The individuals were the units of randomization.

Participants were instructed to abstain from nonsteroidal, anti-inflammatory medication for at least 4 days, from alcoholic beverages for at least 2 days, and from caffeine- or theobromine-containing foods for at least 24 hours before the test and during the test day. The subjects were instructed to maintain low phytochemical intake the evening before the study and to fast from 10 p.m. onwards. [Phytochemicals are components of plants. Examples of foods and beverages which have a high phytochemical content include many fruits, coffee, some teas, green peppers, garlic, onions, yogurt, bran, and cruciferous vegetables such as broccoli, cabbage, and cauliflower.]

Blood was drawn from the subjects prior to consumption of any food. After the initial blood was drawn, the subjects were divided into four groups. One group consumed 81 mg of aspirin (acetylsalicylic acid) (Bayer pediatric aspirin). A second group consumed a high cocoa polyphenol beverage consisting of 18.75 g of procyanidin enriched cocoa powder derived from Sulawesi beans (containing 51.1 mg/g of total procyanidins, 11.2% fat, 0.092% caffeine, 1.618% theobromine) and 12.5 g of sucrose mixed with 300 ml of distilled water. A third group consumed the high cocoa procyanidin beverage and 81 mg of baby aspirin. The final group consumed 81 mg of baby aspirin and a procyanidin deficient cocoa beverage consisting of 18.75 g of cocoa powder (containing 0.45 mg/g total procyanidins, 9.87% fat, 2.063% theobromine, 0.234% caffeine) and 12.5 g of sucrose mixed with 300 ml of distilled water. During the test period the subjects were permitted to consume water, caffeine-free diet soda, bagels, low fat cream cheese, and bananas. Blood was drawn from each of the subjects two hours and six hours post consumption of the treatment. Venous blood was aspirated into evacuated tubes containing 0.5 ml of 3.2% buffered sodium citrate solution.

Inhibition of platelet aggregation was measured using a platelet function analyzer (PFA-100™, Dade Behring International, Miami, Fla.), according to the manufacturer's instructions. The system comprises a microprocessor-controlled instrument and a disposable test cartridge containing a biologically active membrane. The instrument aspirates a blood sample under constant vacuum from the sample reservoir through a capillary and a microscopic aperture cut into the membrane. The membrane is coated with collagen and epinephrine. The presence of these biochemical stimuli, and the high shear rates generated under the standardized flow conditions, result in platelet attachment, activation and aggregation, slowly building a stable platelet plug at the aperture. The time in seconds required to obtain full occlusion of the aperture is reported as the "closure time" (Kundu et al., "Description of an in vitro platelet function analyzer-PFA-100" Semin Thromb Hemost 21 Suppl 2: 106–12, 1995). It is well-known that aspirin treatment results in a reduction in platelet aggregation which causes an increase in closure time as measured by PFA-100 (Marshall et al., "A comparison of the effects of aspirin on bleeding time measured using the Simplate method and closure time measured using the PFA-100, in healthy volunteers", Br J Clin Pharmacol 44:151–155, 1997).

The results show that, at the two hour time point, all four treatments resulted in an increase in closure time compared to the base-line level ($p<0.05$). Furthermore, a comparison between the aspirin and cocoa plus aspirin treatments shows a difference between the closure times of the two treatments ($p<0.08$). This demonstrates that combining aspirin with cocoa procyanidin oligomers enhances the ability of the aspirin to inhibit platelet activation. There is no difference between closure times subsequent to treatment with aspirin alone and with aspirin plus CP-deficient cocoa, showing that the enhanced effect is dependent upon the presence of the procyanidins in the cocoa. The results also demonstrate that the aspirin plus cocoa and aspirin plus CP-deficient cocoa treatments differ significantly in their closure times ($p<0.06$), confirming that the enhanced effects of the cocoa/aspirin combination depend upon the presence of the procyanidins.

The blood samples were also analyzed for changes in leukotriene, prostacyclin and thromboxane levels resulting from the four treatment regimes. Immunoassay procedures were conducted as described by Westcott et al, "Analysis Of 6-Keto PGF1 Alpha, 5-HETE, And LTC4 In Rat Lung: Comparison Of GM/MS, RIA and EIA", Prostaglandins 32:857–873, 1986; Yakota et al, "Enzyme Immunoassay Of Prostanoids In Blood And Urine", Adv. Prostgl.Thrombox. Leukot. Res. 15:33–34, 1985; and Schramm et al, "Differential Effects of Small and Large Molecular Weight Phytochemicals on Endothelial Cell Eicosanoid Secretion" J Agric Food Chem 46:1900–1905, 1998. The prostacyclin ($PGI_2$) metabolite 6-keto prostaglandin F1-alpha was measured with Cayman enzyme immunoassay #515211, the thromboxane ($TXA_2$) metabolite $TXB_2$ was measured with Cayman enzyme immunoassay 519031, and leukotrienes C4, D4 and E4 were quantified using the immunoassay EA-39 from Oxford Biomedical Research. P values were calculated using the paired sample T-test. Values of p<0.05 were considered to be statistically significant. The data from the eicosanoids studies is presented in Table 1 and FIG. 1. All treatments apart from aspirin plus procyanidin-deficient cocoa result in a drop in the ratio of atherogenic to atherostatic eicosanoids, showing that all treatments are beneficial for vascular health and the prevention of ischaemic attacks and that the increase in closure time afforded by the treatments are at least in part due to modulation of the eicosanoids. The results show that the CP rich cocoa plus aspirin causes a reduction in the levels of the atherogenic leukotrienes, and an increase in the levels of atherostatic prostacyclin. In comparison, the CP-deficient cocoa plus aspirin treatment resulted in a decrease in prostacylin levels and an increase in leukotriene levels. These results show that the atherostatic effects of the cocoa are dependent upon the presence of the procyanidins.

Interestingly, these results suggest that the mechanisms which result in an antiplatelet activity are different for the aspirin and high cocoa procyanidin cocoa treatments. The mechanism of action of aspirin is via an inhibition of the arachidonic acid pathway (by inhibiting prostaglandin production) which results in a drop in thromboxane levels, leading to a prevention of thromboxane dependent platelet activation. This accounts for the anti-thrombotic effects of aspirin. As can be seen in Table 1, all three treatments involving aspirin result in a significant reduction in plasma thromboxane levels at both two and six hours post-consumption of the treatment, whereas the high cocoa procyanidin cocoa treatment does not alter plasma thromboxane levels. This is confirmed by the results which show that the combined high cocoa procyanidin and aspirin treatment does not result in a decrease in thromboxane levels below that which was achieved by the aspirin only treatment. In contrast to these results, the PFA-100 data reveals that combined treatment with high cocoa procyanidin cocoa and aspirin results in an increase in closure time over each of the individual treatments, i.e., the treatment effects are enhanced.

Therefore, the antiplatelet activity of the cocoa procyanidins does not appear to be dependent upon an inhibition of the arachidonic acid pathway. There are two significant implications of this fact. Firstly, the adverse effects which have been documented for aspirin, which are resultant from the inhibition of the arachidonic acid pathway, would not be caused by treatment with the cocoa procyanidins. Secondly, treatment with the combination is likely to result in a synergistic antiplatelet effect with each of the components (aspirin and cocoa procyanidin rich cocoa) contributing to antiplatelet activity by a different mechanism.

In summary, the treatment with the combination of aspirin and cocoa procyanidin-enriched cocoa results in a decrease in platelet activity which is additive and probably synergistic There is also evidence that the co-administration of cocoa and aspirin enhances the activity of the aspirin, allowing the use of much lower doses to achieve comparable efficacy of the drug, whilst minimizing the harmful side-effects of the aspirin.

EXAMPLE 3

The Effects of the Consumption of a Procyanidin Rich Beverage in Combination with Aspirin on Platelet Activity.

The effects of consumption of a cocoa beverage in combination with an effective amount of aspirin on platelet activation were studied.

The subjects used in the previous study also participated in the surface protein expression study. The methodology with respect to treatment regimes and collection of blood was identical to that which was outlined in the previous example.

Within 10 minutes of draw, whole blood was incubated in polystyrene tubes for 5 minutes at room temperature with 10 $\mu$m HEPES buffer (pH 7.4, unstimulated control), 20 or 100 $\mu$m ADP or 20 $\mu$tm epinephrine (BioData, Horsham, Pa.) in the presence or absence of the peptide Arg-Gly-Ser (Sigma, St. Louis, Mo.). After 5 minutes, samples were suspended in 1 ml HEPES buffer and 100 $\mu$m of sample were transferred to tubes containing saturating concentrations (20 $\mu$m) each of the following fluorescent-labeled monoclonal antibodies: PAC1-fluorescein isothiocyanate (FITC), anti-CD62P-phycoerythrin (PE) and anti-CD42a-PerCP. PAC1 recognizes the activated conformation of the fibrinogen-binding receptor GPIIb-IIIa and anti-CD62P recognizes P-selectin, present on the surface of activated platelets. Anti-CD42a recognizes GP1b-1X, which is on the surface of both activated and resting platelets. Mouse IgG, FITC and mouse IgG, PE were used as isotype controls. The Arg-Gly-Asp-Ser-peptide was used to block binding of the PAC1 antibody to platelets and thus set the negative control marker on the flow cytometer. Antibodies and isotype controls were purchased from Becton Dickinson Immunocytometry Systems, Inc., San Jose, Calif.

Whole blood samples in the presence and absence of the agonists ADP and epinephrine were incubated with monoclonal antibodies or isotype control for 20 minutes in the dark at room temperature. Samples were then fixed in filtered 1% paraformaldehyde (pH 7.2) and stored in the dark at 2–8° C. All samples were analyzed within 48 hours on a FACScan flow cytometer using LYSYS II software. The flow cytometer performance was verified using 1, 2 and 10 $\mu$m calibration beads (Becton Dickinson Immunocytometry Systems, Inc., San Jose, Calif. and Flow Cytometry Systems, Research Triangle Park, N.C.). Twenty thousand events were collected in list mode with all light-scatter and fluorescence parameters in logarithmic code. Platelets were gated on the basis of lightscatter and CD42a expression. Activated platelets were defined as the percentage of CD42a positive events coexpressing the activated conformation of GPIIb-IIa or P-selectin. Platelet microparticles were defined as the percentage of CD42a positive events less than 2 $\mu$m in size.

To perform the statistical analysis of the results, Friedman's repeated measures ANOVA on ranks (RM ANOVA on ranks) was used to compare the baseline, 2 and 6 hour results in each treatment group. Tukey's all pairwise comparison was used for post hoc multiple comparisons. A P values less than 0.05 was considered significant. The platelet-dependent hemostasis data were also analyzed for statistical differences among treatment groups for each time point, baseline, 2 and 6 hour.

Results

Figure 2:
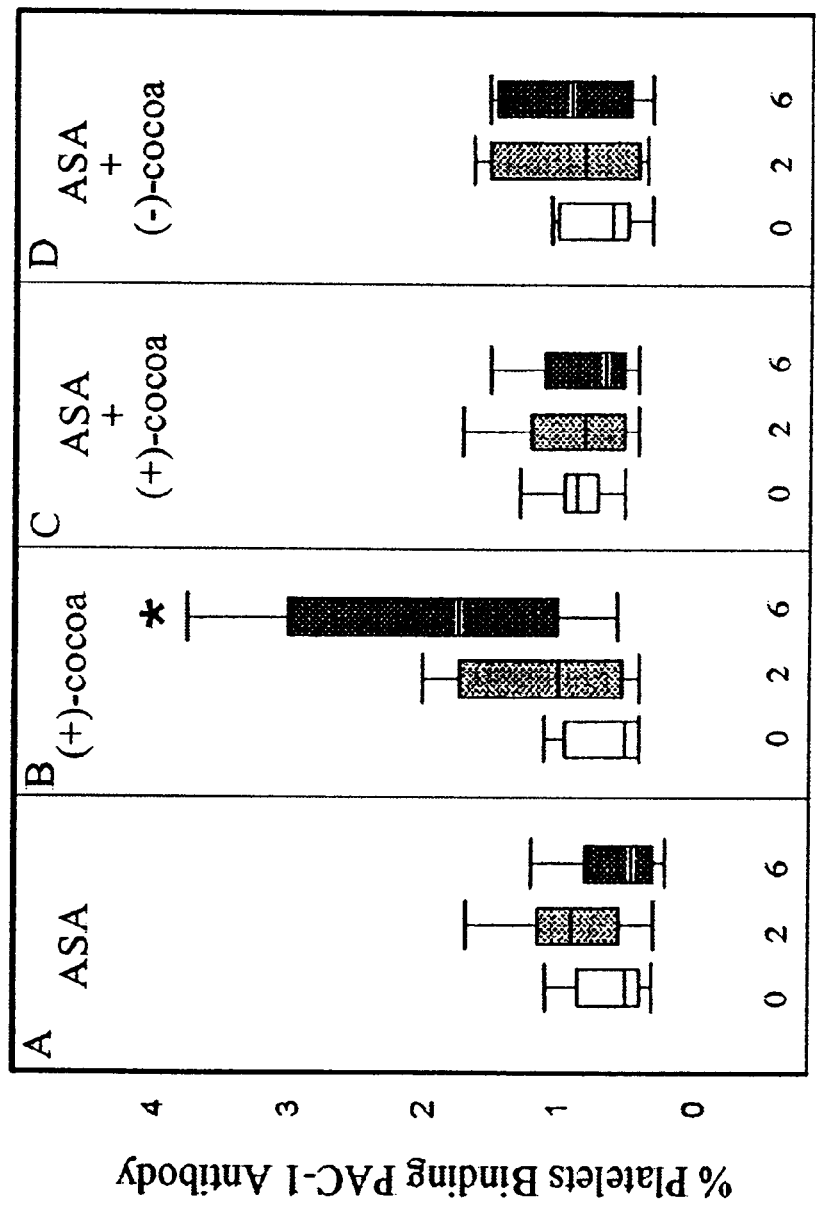
FIG. 2A–D represents comparative unstimulated platelet IIb/IIIa receptor expression among the four treatments: aspirin, (+)-cocoa, aspirin in combination with (+)-cocoa, and aspirin in combination with (−)-cocoa recorded at two time intervals.
Figure 3:
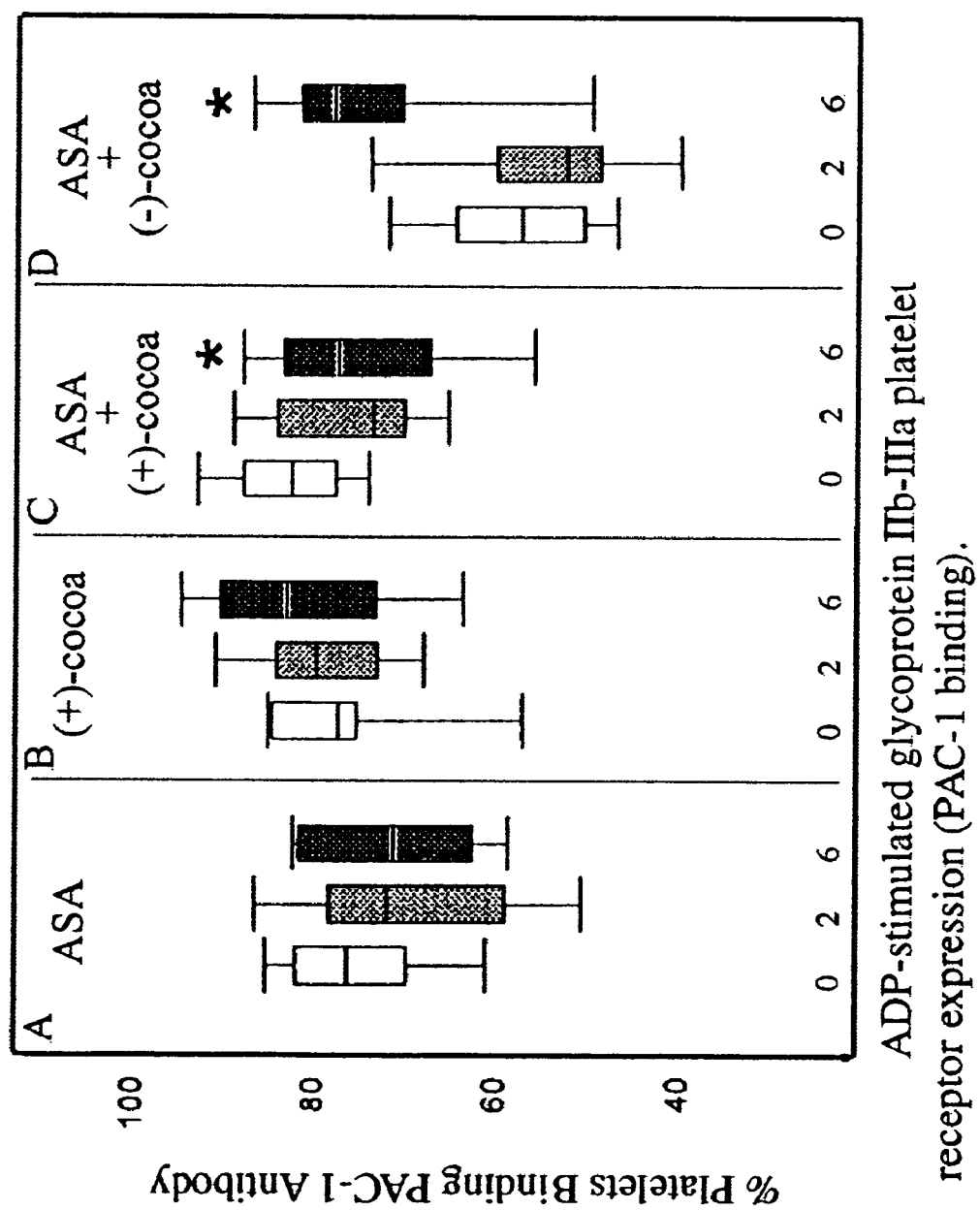
FIG. 3A–D represents comparative ADP-stimulated platelet IIb/IIIa receptor expression among the four treatments: aspirin, (+)-cocoa, aspirin in combination with (+)-cocoa, and aspirin in combination with (−)-cocoa recorded at two time intervals.
Figure 4:
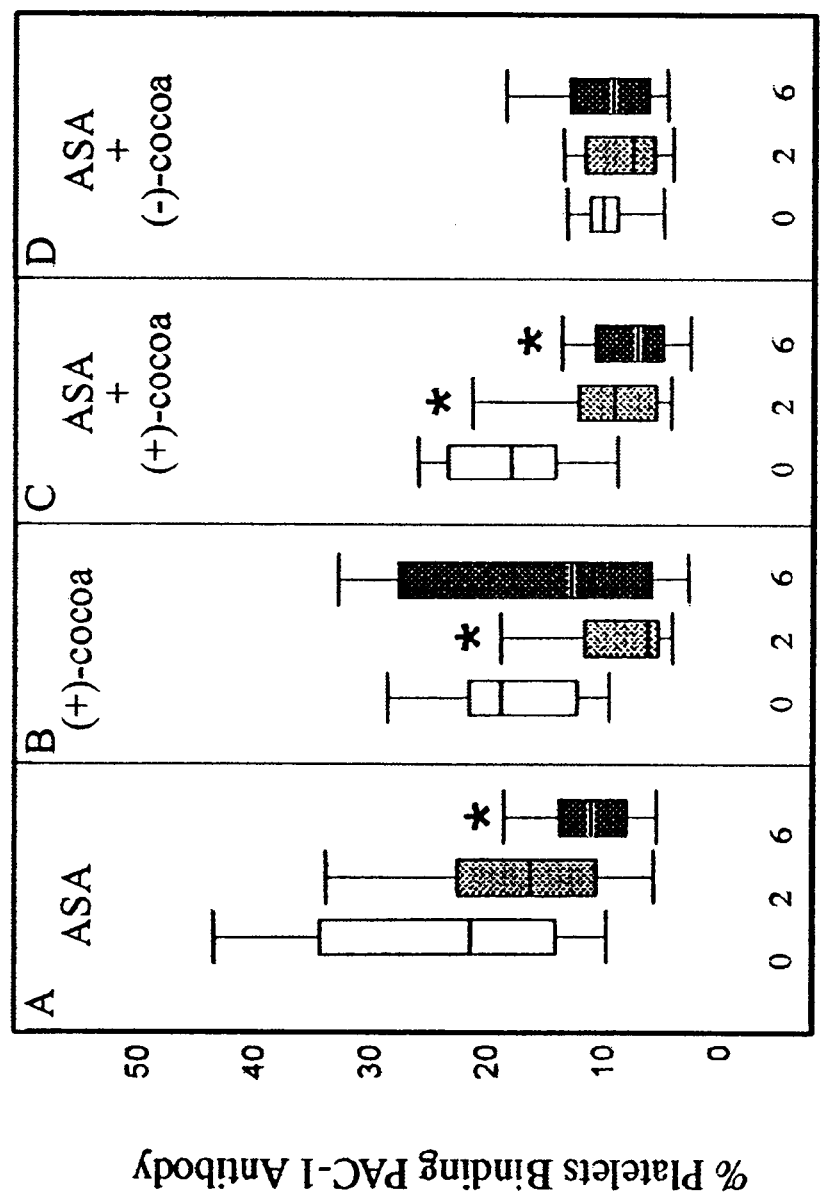
FIG. 4A–D represents comparative epinephrine-stimulated platelet IIb/IIIa receptor expression among the four treatments: aspirin, (+)-cocoa, aspirin in combination with (+)-cocoa, and aspirin in combination with (−)-cocoa recorded at two time intervals.

The effects of cocoa and aspirin consumption on the ex vivo expression of the activated conformation of the GPIIb/IIIa platelet receptor, with and without stimulation by the weak agonists ADP and epinephrine are shown in FIGS. 2, 3, and 4.

Upon platelet activation, the GPIIb/IIIa receptor undergoes a conformational change rendering it capable of binding fibrinogen and von Willebrand factor. The formation of interplatelet bridges through ligand binding to activated GPIIb/IIIa receptors is essential to platelet aggregation and thrombus formation.

Referring to FIG. 2B, (+)-Cocoa consumption increased unstimulated GPIIb/IIIa expression at 6 hours as compared to baseline (P<0.001). None of the other treatments significantly affected unstimulated GPIIb/IIIa expression Referring to FIG. 3C, ADP-induced GPIIb/IIIa expression was suppressed 6 hours following consumption of ASA+ (+)-cocoa compared to baseline (P=0.004). In contrast, as shown in FIG. 3D, the consumption of ASA+(−)-cocoa increased the expression of ADP-induced GPIIb/IIIa expression at 6 hours as compared to either baseline or 2 hours (P=0.005). As shown in FIG. 4A, ASA consumption suppressed epinephrine-induced GPIIb/IIIa expression at 6 hours compared to baseline (P=0.003). Consumption of (+)-cocoa suppressed epinephrine-induced GPIIb/IIIa expression at 2 hours as compared to baseline (P=0.005; FIG. 4B). The combined consumption of ASA+(+)-cocoa suppressed epinephrine-induced GPIIb/Ill expression at both 2 and 6 hours compared to baseline (P=0.006; FIG. 4C). In contrast, there was no significant change in epinephrine-induced GPIIb/IIIa expression following consumption of ASA+(−)-cocoa (FIG. 4D).

The effects of cocoa and aspirin consumption on the ex vivo platelet surface expression of P-selectin (CD62), with or without stimulation by the weak agonists ADP and epinephrine, are shown in Table 2. P-selectin is expressed on the surface of activated platelets. None of the treatments significantly affected unstimulated P-selectin expression. Consumption of ASA+(−) −cocoa was the only treatment that suppressed ADP-induced P-selectin expression at 2 hours (P=0.001).

Consumption of ASA suppressed epinephrine-induced P-selectin expression at 6 hours compared to baseline (P=0.028), whereas (+)-cocoa had no effect. The combined consumption of ASA+(+)-cocoa suppressed epinephrine-induced P-selectin expression at 2 and 6 hours compared to baseline (P=0.014). In contrast, the combined consumption of ASA+(−)-cocoa produced no significant change in epinephrine-induced P-selectin expression.

EXAMPLE 4

Tablet Formulations

A tablet formulation is prepared using high cocoa procyanidin cocoa solids obtained by methods described in the U.S. Pat. No. 6,015,913, hereby incorporated herein by reference. Briefly, this edible material is prepared by a process which enhances the natural occurrence of the cocoa procyanidins in contrast to their levels found in traditionally processed cocoa, such that the ratio of the initial amount of the cocoa procyanidins found in the unprocessed bean to that obtained after processing is less than or equal to 2. For simplicity, this cocoa solids material is designated herein as CP-cocoa solids.

A tablet formula comprises the following (percentages expressed as weight percent):

| | |
|---|---|
| CP-cocoa solids | 24.0% |
| 4-Fold Natural vanilla extract (Bush Boake Allen) | 1.5% |
| Magnesium stearate (dry lubricant) (AerChem, Inc.) | 0.5% |
| Dipac tabletting sugar (Amstar Sugar Corp.) | 37.0% |
| Xylitol (American Xyrofin, Inc.) | 37.0% |
| Aspirin | 50 mg |

The CP-cocoa solids and vanilla extract are blended together in a food processor for 2 minutes. The aspirin, sugars and magnesium stearate are gently mixed together, followed by blending in the CP-cocoa solids/vanilla mix. This material is run through a Manesty Tablet Press (B3B) at maximum pressure and compaction to produce round tablets (15 mm×5 mm) weighing 1.5–1.8 gram.

Alternatively, CP is used in the form of an extract containing about 600 mg] total procyanidin monomers and oligomers.

A person of skill in the art can readily prepare other tablet formulas covering a wide range of flavors, colors, excipients, vitamins, minerals, OTC medicaments, sugar fillers, UV protectants (e.g., titanium dioxide, colorants, etc.), binders, hydrogels, and the like except for polyvinyl pyrrolidone which would irreversibly bind the cocoa procyanidins or combination of compounds. The amount of sugar fillers may be adjusted to manipulate the dosages of the cocoa procyanidins or combination of compounds.

EXAMPLE 5

Capsule Formulations

A variation of the tablet disclosed in Example 4, oral dosage form comprising a cocoa procyanidin in combination with aspirin is made with push-fit capsules made of gelatin, as well as soft sealed capsules made of gelatin and a plasticizer such as glycerol. The push-fit capsules contain the compound of the invention or combination of compounds or CP-cocoa solids as described in Example 4 in the form of a powder which can be optionally mixed with fillers such as lactose or sucrose to manipulate the dosages of the cocoa procyanidins. In soft capsules, the isolated cocoa procyanidins or CP-cocoa solids are suspended in a suitable liquid such as fatty oils or cocoa butter or combinations therein. The capsule may contain UV protectants such as titanium dioxide or suitable colors to protect against UV. The capsules can also contain fillers such as those mentioned in Example 4.

EXAMPLE 6

Methylated Procyanidins

The effects of methylated cocoa procyanidins on vascular smooth muscle is shown in this example. An in vitro method that measures endothelium dependent relaxation (EDR) in rabbit aortic rings was used.

Preparation of Cocoa Polyphenols and Procyanidin Metabolites.

Methylated tetramer was prepared by reacting the purified cocoa procyanidin tetramer fraction (isolated as described in the U.S. Pat. No. 5,554,645 to Romanczyk et al.) Wit a diazomethane reagent.

To prepare the diazomethane reagent, a Diazald Kit Diazomethane Generator (Aldrich Chemicals) was used. The reaction consists of two reagents. For the first reagent, 5 g of KOH was dissolved in 8 mL of water, then 10 mL of MeOH was added. The reagent was placed in a round bottom flask to be used as the reaction vessel. This reaction vessel was attached to a condenser and a receiving flask which was cooled in an ice bath. An ether trap was placed at the side-arm. The second reagent was prepared by dissolving 5 g of Diazald in 45 mL of re-distilled diethyl ether. This reagent was placed in a separatory finnel over the reaction vessel. The reaction vessel was warmed to 65° C. using a water bath. The Diazald solution was dripped into the KOH solution at a rate which is equivalent to the rate of distillation. When the Diazald was used up, the separatory funnel was rinsed with 10 mL of ether.

100 mg of tetramer was suspended in 3 mL of methanol. 12 mL of the diazomethane reagent was added. The mixture reacted for 20 minutes at room temperature, then left to react overnight (16 hours) in the freezer (−7° C.). The reaction was stopped by adding 2.5 mL of 10% acetic acid in methanol. The solvent was removed under a stream of nitrogen and the solids dried under vacuum.

The reaction was monitored using API-ES mass spectrometry in the negative ion mode. 10 $\mu$L was injected using a flow rate of 1 mL/min composed of 8% 10 mM ammonium acetate in methanol and 92% methanol. Ionization was achieved using a capillary voltage of 3500 V and a fragmentation voltage of 100 V. Spectra were scanned over a mass range of m/z 500–1500. Mass spectral data indicated that at the end of the reaction, no unmethylated tetramer remained. The majority of the reaction products were methylated at 14–18 of the hydroxyl positions. Some of the tetramer is completely methylated at all 20 positions.

Endothelium Dependent Relaxation.

Male New Zealand White rabbits (2.5–3 kg weight) were terminally anaesthetized with pentobarbital (50 mg/kg). The thoracic aorta was excised and carefully cleaned of adhering fat and connective tissue. The aorta was then cut into rings (3–4 mm length), mounted in conventional 20 ml organ baths filled with Krebs-bicarbonate buffer (m Mol/l): NaCl 116.0, KCl 5.4, $CaCl_2$ 1.2, $NaHCO_3$ 22.0, $NaH_2PO_4$ 1.2, $MgCl_2$ 1.2 and glucose 10.1), maintained at 37° C., pH 7.4 and continuously aerated with a 95% $O_2$—5% $CO_2$ mixture. The tissues were connected to a force displacement transducer (Grass Instrument Co., Quincy Mass. Model FT03C), and stretched to a basal tension of 8 g.

The rings were equilibrated in the organ baths for a period of 90 min after which they were pre-contracted with norepinephrine ($10^{-5}$ M). The presence of functional endothelium was assessed in all preparations by the ability of acetylcholine ($10^{-5}$ M) to induce 40% or more relaxation of the pre-contracted rings. These procedures have been previously published in detail (Kappagoda, Cardiovascular Res. 25: 270–82, 1991). Aortic rings with functional endothelium were pre-contracted with norepinephrine ($10^{31\ 5}$ M). When the contraction reached a steady state, the methylated tetramer was added at concentrations of $10^{-3}$, $10^{-4}$, $10^{-5}$, $10^{-6}$, $10^{-7}$ and $2.5 \times 10^{-4}$. The results are shown in Table 3. The results from 4 separate aortic rings show that the methylated tetramer has a relaxant effect. Therefore, these derivatives are effective as the parent compounds in their ability to maintain vascular health and treat vascular disease.

TABLE 3

Dose response relaxation by methylated tetramer for 4 separate rabbit aortic ring

| Dose methylated tetramer (M) | % relaxation ring #1 | % relaxation ring #2 | % relaxation ring #3 | % relaxation ring #4 |
|---|---|---|---|---|
| $10^{-7}$ | 0 | 6.1 | 2.9 | 0 |
| $10^{-6}$ | 7.5 | 24.2 | 14.7 | 16 |
| $10^{-5}$ | 30 | 27.3 | 17.6 | 16 |
| $10^{-5}$ | 50 | 27.3 | 17.6 | 20 |
| $2.5 \times 10^{-4}$ | | | | 40 |
| $10^{-3}$ | | | | 48 |

TABLE 1

|  | Aspirin | Cocoa | Cocoa + Aspirin | (−)-Cocoa + Aspirin |
|---|---|---|---|---|
| 2 hrs |  |  |  |  |
| Prostacyclin | 103 | 107 | 104 | 95 |
| Thromboxane | 91 | 99 | 92 | 89 |
| Leukotrienes | 101 | 100 | 97 | 105 |
| LT/PG12 ratio | 99 | 93 | 94 | 112 |
| TXB2/PG12 ratio | 89 | 89 | 88 | 95 |
| 6 hrs |  |  |  |  |
| Prostacyclin | 104 | 107 | 102 | 77 |
| Thromboxane | 89 | 99 | 91 | 79 |
| Leukotrienes | 100 | 99 | 99 | 94 |
| LT/PG12 ratio | 100 | 93 | 96 | 120 |
| TXB2/PG12 ratio | 86 | 89 | 88 | 94 |

TABLE 2

Effect of Aspirin and Cocoa Procyanidin Consumption on Platelet Expression of Activated P-Selectin (CD62P)
% CD62 + Platelets
Median (Range)

| Treatment | Unstimulated | | | 20 $\mu$M ADP | | | 20 $\mu$M Epinephrine | | |
|---|---|---|---|---|---|---|---|---|---|
|  | 0 Hour | 2 Hour | 6 Hour | 0 Hour | 2 Hour | 6 Hour | 0 Hour | 2 Hour | 6 Hour |
| ASA | 1.4 | 1.5 | 1.3 | 64.5 | 60.3 | 60.8 | 7.9 | 6.2 | 4.7* |
|  | (0.6–3.9) | (0.6–4.2) | (0.5–2.9) | (52.1–81.2) | (41.1–81.6) | (43.4–78.1) | (2.5–31.2) | (1.0–34.6) | (1.0–14.6) |
| (+)-cocoa | 1.2 | 1.6 | 1.5 | 60.0 | 58.5 | 65.8 | 6.1 | 5.3 | 8.2 |
|  | (0.6–1.9) | (0.7–3.0) | (0.8–5.7) | (47.1–75.6) | (50.7–81.5) | (50.6–78.6) | (1.2–9.1) | (0.7–13.9) | (1.1–15.3) |
| ASA + (+)-cocoa | 1.6 | 1.2 | 1.3 | 67.3 | 62.8 | 61.0 | 4.6 | 3.1* | 2.4* |
|  | (0.6–3.9) | (0.7–2.7) | (0.6–2.9) | (48.1–83.3) | (39.7–82.1) | (39.2–77.3) | (1.8–15.6) | (0.8–7.4) | (1.0–12.4) |
| ASA + (−)-cocoa | 1.3 | 1.4 | 1.5 | 58.0 | 52.1* | 61.1 | 3.6 | 3.8 | 4.3 |
|  | (0.6–1.8) | (0.5–1.9) | (0.7–3.8) | (44.7–74.7) | (35.3–69.1) | (49.3–77.7) | (0.9–6.9) | (1.6–9.2) | (1.6–8.8) |

What is claimed is:

1. A composition for oral administration comprising an acetylsalicylic acid and a cocoa procyanidin in a combined effective amount to treat or prevent platelet dysfunction, wherein the amount of acetylsalicylic acid in the combined effective amount is less than an amount of acetylsalicylic acid utilized when acetylsalicylic acid is administered alone, and the amount of cocoa procyanidin is effective to increase the levels of prostacyclin in the body of a subject.

2. The composition of claim 1, wherein the amount of acetylsalicylic acid is less than 80 mg.

3. The composition of claim 1, wherein the amount of acetylsalicylic acid is less than 70 mg.

4. The composition according to claim 1 which is a food, a dietary supplement or a food additive.

5. The composition according to claim 1 wherein the cocoa procyanidin is a monomer.

6. The composition according to claim 1 wherein the cocoa procyanidin is a dimer.

7. The composition according to claim 1 wherein the cocoa procyanidin comprises an oligomer.

8. The composition according to claim 7 wherein the oligomer is a cocoa procyanidin oligomer 2 to 18 or a mixture thereof.

9. A composition comprising an acetylsalicylic acid and a cocoa procyanidin in a combined effective amount to treat or prevent platelet dysfunction, wherein the amount of acetylsalicylic acid in the combined effective amount is less than an amount of acetylsalicylic acid utilized when acetylsalicylic acid is administered alone, and the amount of cocoa procyanidin is effective to increase the levels of prostacyclin in the body of a subject upon administration, and wherein the cocoa procyanidin is present in a cocoa ingredient having an enhanced or conserved level of cocoa procyanidins.

10. A composition according to claim 9 wherein the cocoa ingredient derives from cocoa beans having a fermentation factor of 275 or less.

11. A composition according to claim 9 wherein the cocoa ingredient comprises cocoa solids which are obtainable by:
    (a) heating cocoa beans to an internal bean temperature which is just sufficient to reduce the moisture content to about 3% by weight and to loosen the cocoa shell;
    (b) winnowing the cocoa nibs from the cocoa shells;
    (c) screw pressing the cocoa nibs; and
    (d) recovering the cocoa butter and partially defatted cocoa solids which contain cocoa procyanidins.

12. The composition according to claim 9 wherein the cocoa ingredient is a beverage mix.

13. A pharmaceutical composition comprising an acetylsalicylic acid and a cocoa procyanidin in a combined effective amount to treat or prevent platelet dysfunction, wherein the amount of acetylsalicylic acid in the combined effective amount is less than an amount of acetylsalicylic acid utilized when acetylsalicylic acid is administered alone, and the amount of cocoa procyanidin is effective to increase the levels of prostacyclin in the body of a subject.

14. A method of treating or preventing a condition associated with platelet dysfunction comprising administering to a subject in need thereof a cocoa procyanidin and acetylsalicylic acid in a combined effective amount to treat or prevent the platelet dysfunction, wherein the amount of acetylsalicylic acid in the combined effective amount is less than an amount of acetylsalicylic acid utilized when acetylsalicylic acid is administered alone, and the amount of cocoa procyanidin is effective to increase the levels of prostacyclin in the body of the subject.

15. The method of claim 14, wherein the subject is a human.

16. The method of claim 15, wherein the amount of acetylsalicyic acid is less than 80 mg/day.

17. The method of claim 15, wherein the amount of acetylsalicyic acid is less than 70 mg/day.

18. The method of claim 14, wherein the cocoa procyanidin is a monomer.

19. The method of claim 14, wherein the cocoa procyanidin is a dimer.

20. The method of claim 14, wherein the cocoa procyanidin comprises an oligomer.

21. The method of claim 14, wherein the cocoa procyanidin and the acetylsalicylic acid are administered in the same composition.

22. The method of claim 14, wherein the cocoa procyanidin and the acetylsalicylic acid are administered separately.

23. A method of treating or preventing a condition associated with platelet dysfunction comprising administering to a subject in need thereof a cocoa procyanidin derivative and acetylsalicylic acid in a combined effective amount to treat or prevent the platelet dysfunction, wherein the amount of acetylsalicylic acid in the combined effective amount is less than an amount of acetylsalicylic acid utilized when acetylsalicylic acid is administered alone, and the amount of cocoa procyanidin derivative is effective to increase the levels of prostacyclin in the body of a subject.

24. The method of claim 23, wherein the cocoa procyanidin derivative is a methylated cocoa procyanidin.

25. The method of claim 23, wherein the cocoa procyanidin derivative is a gallated cocoa procyanidin.

* * * * *